US006100277A

United States Patent [19]

Tucker et al.

[11] Patent Number: 6,100,277
[45] Date of Patent: *Aug. 8, 2000

[54] RETROVIRAL PROTEASE INHIBITOR COMBINATIONS

[75] Inventors: Simon P Tucker, Ellisville, Mo.; Martin L Bryant, Los Altos, Calif.; Karen E Potts, St. Louis; Mary L Smidt, Ballwin, both of Mo.

[73] Assignee: G.D. Searle & Co., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/458,154

[22] Filed: Jun. 2, 1995

Related U.S. Application Data

[63] Continuation of application No. 08/253,638, Jun. 3, 1994, abandoned.

[51] Int. Cl.[7] .......................... A01N 43/42; A01N 37/28; A01N 43/54; A01N 43/40

[52] U.S. Cl. .......................... 514/311; 514/507; 514/256; 514/277; 514/365; 514/473; 514/218; 514/49

[58] Field of Search ...................................... 514/507, 311, 514/256, 271, 365, 473, 218, 49

[56] References Cited

U.S. PATENT DOCUMENTS

| | | | |
|---|---|---|---|
| H1649 | 5/1997 | Barrish et al. | 514/210 |
| 4,644,055 | 2/1987 | Kettner et al. | 530/330 |
| 4,652,552 | 3/1987 | Kettner et al. | 514/18 |
| 4,857,511 | 8/1989 | Rideout et al. | 514/50 |
| 5,122,517 | 6/1992 | Vince et al. | 514/50 |
| 5,157,041 | 10/1992 | Handa et al. . | |
| 5,413,999 | 5/1995 | Vacca et al. | 514/231 |
| 5,458,889 | 10/1995 | Bourbon et al. | 424/673 |
| 5,476,874 | 12/1995 | Hungate et al. | 514/252 |
| 5,484,926 | 1/1996 | Dressman et al. | 546/114 |
| 5,504,104 | 4/1996 | Elsworth et al. | 514/455 |
| 5,527,799 | 6/1996 | Vacca et al. | 514/252 |
| 5,585,397 | 12/1996 | Tung et al. | 514/473 |

FOREIGN PATENT DOCUMENTS

| | | |
|---|---|---|
| 0337714A2 | 10/1989 | European Pat. Off. . |
| 342541A2 | 11/1989 | European Pat. Off. . |
| 346847 | 12/1989 | European Pat. Off. . |
| 346847A2 | 12/1989 | European Pat. Off. . |
| 0393445A2 | 10/1990 | European Pat. Off. . |
| 0402646A1 | 12/1990 | European Pat. Off. . |
| 0 541 168 A1 | 5/1993 | European Pat. Off. ..... A61K 31/495 |
| 0 580 402 A2 | 7/1993 | European Pat. Off. . |
| 617968 | 10/1994 | European Pat. Off. . |
| 0 691 345 A2 | 1/1996 | European Pat. Off. .......... C07K 5/02 |
| 0 691 345 A3 | 2/1999 | European Pat. Off. .......... C07K 5/02 |
| 2209752A | 5/1989 | United Kingdom . |
| WO 92/08688 | 5/1992 | WIPO . |
| 93/09096 | 5/1993 | WIPO . |
| WO 96/04913 | 2/1996 | WIPO . |
| WO 97/01349 | 1/1997 | WIPO . |

OTHER PUBLICATIONS

Merry, et al., "Saquinavir Pharmacokinetics Alone and in Combination With Ritonavir in HIV–Infected Patients," F29–F33, 1997.

Richman, et al., "Protease Uninhibited," Nature, vol. 374, 1995.

Barry, et al., "Protease Inhibitors in Patients with HIV Disease Clinically Important Pharmacokinetic Consideration," Pharmaceokinetic–Pharmacodynamic Relationships, pp. 194–209, 1997.

Abstract No. 245, "Efficacy and safety of Quadruple Combination Therapy in Treatment Experienced HIV/AIDS Patient," 4th Conf Retro and Opportun Infect, Jan. 22–26, 1997, p. 103.

Abstract No. 209, "Selection and Analysis of HIV–1 Variants With Increased Resistance to ABT–378, A Novel Protease Inhibitor," 4th Conf Retro and Opportun Infect, Jan. 22–26, 1997, p. 103.

Abstract No. 199, "'Salvage Therapy'Using the Combination of Ritonavir and Saquinavir in Patients with Advanced HIV Infection," 4th Conf Retro and Opportun Infect, Jan. 22–26, 1997, p. 101.

Abstract No. 257, "The Use of Antiretroviral Therapy in Association With Evolving Standards of Practice," 4th Conf Retro and Opportun Infect, Jan. 22–26, 1997, p. 111.

Abstract No. 609, "Pharmacokinetics/pharmacodynamics of Ritonavir–Saquinavir Combination Therapy," 4th Conf Retro and Opportun Infect, Jan. 22–26, 1997, p. 177.

Abstract No. Th.B. 934, "Combination Use of Ritonavir and Saquinavir in HIV–Infected Patients: Preliminary Safety and Activity Data," Int Conf Aids (United States), Jul. 7–12, 1996 (Program Supplement, p. 20).

Abstract, "Saquinavir Pharmacokinetics Alone and in Combination With Ritonavir in HIV–Infected Patients," United Kingdom, AIDS (1997) Nov. 4.

Abstract, "Ritonavir," Bioorganic and Medicinal Chemistry, (1997) 5/3 (461–462).

Abstract. "Protease Inhibitors in Patients With HIV Disease. Clinically Important Pharmacokinetic Considerations," Clinical Pharmacokinetics, (1977) 32/3 (194–209).

El–Farrash et al., "Generation and Characterization of a Human Immunodeficiency Virus Type 1 (HIV–1) Mutant Resistant to an HIV–1 Protease Inhibitor", Journal of Virology, Jan. 1994, pp. 233–239.

(List continued on next page.)

*Primary Examiner*—Marianne M. Cintins
*Attorney, Agent, or Firm*—Banner & Witcoff, Ltd.

[57] ABSTRACT

The present invention is directed to a method for the treatment of mammalian retrovirus infections, such as HIV, using combinations of retroviral protease inhibitors which are effective in preventing the replication of the retroviruses in vitro or in vivo. This invention, in particular, relates to protease inhibitor compounds used in combination therapy with other protease inhibitor compounds. This invention also relates to combination therapy with a combination of protease inhibitors and antiviral agents other than protease inhibitors.

8 Claims, No Drawings

OTHER PUBLICATIONS

Lang, M., *Archiv der Pharmazie,* vol. 326(9) (1993) p. 574.

Fischl, "Combination Antiretroviral Therapy for HIV Infection" *Hospital Practice,* Jan. 15, 1994, pp. 43–48.

Larder et al., "Potential Mechanism for Sustained Antiretroviral Efficacy of AZT–3TC Combination Therapy", *Science* 269:696–699 (1995).

Patick et al., "Characterization of a Human Immunodeficiency Virus Type 1 Variant with Reduced Sensitivity to an Aminodiol Protease Inhibitor", *J. Virology* 69(4):2148–2152 (1995).

Hirsch et al., "Therapy for Human Immunodeficiency Virus Infection", *New England J. Med.,* 328(23):1686–1695 (1993).

Getman et al., "Discovery of a Novel Class of Potent HIV–1 Protease Inhibitors Containing the (R)–(Hydroxyethyl)urea Isostere", *J. Med. Chem.* 36:288–291 (1993).

Tam et al., "Intriguing Structure–Activity Relations Underlie the Potent Inhibition of HIV Protease by Norstatine–Based Peptides", *J. Med. Chem.* 35:1318–1320 (1992).

Clare et al., "Preparation of N–(3–hydroxy–1–phenyl–4–urei=do–2–butyl)asparaginamidesand Analogs as Retroviral Protease Inhibitors", *Chem. Abst.* 738:117:251771f (1992).

Doerr et al., "Neue Entwicklungen in der Antiviralen Chemotherapie", PZ Prisma 1:36–45 (1994).

Merck Index, 10th Ed., 1984, #3092.

Condra et al., "In vivo Emergence of HIV–1 Variants Resistant to Multiple Protease Inhibitors", *Nature* 374:569–571 (1995).

Roberts et al, *Science,* 248, 358–361, (1990).

Erickson et al, *Science,* 249, (1990).

Waldholz, *The Wall Street Journal,* p. B3, Feb. 25, 1994.

Vacca et al, Proc. Natl. Acad. Sci. USA, 91:4096–4100 (1994).

Ho et al, *J. Virol.,* 68:2016–2020 (1994).

Sardana et al, *Biochem.,* 33:2004–2010 (1994).

Loeb et al, *Nature,* 340:397–400 (1989).

Tet. Lett., 35:673–676 (1994).

*Drugs of the Future,* 16(3), 210–212 (1991).

Kagayama et al, *Antimicrobial Agents and Chemotherapy* 1993, 810–817.

Lam et al, "De Novo Design and Discovery of Potent, Nonpeptidal HIV–1 Protease Inhibitors", paper 96 at the 205th American Chemical Society National Meeting, Medicinal Chemistry Division, Denver, CO, Mar. 28–Apr. 2, 1993.

Dorsey et al, "L–735, 524: The Rational Design of a Potent and Orally Bioavailable HIV Protease Inhibitor", paper 6 at the 206th American Chemical Society National Meeting, Medicinal Chemistry Division, Chicago, IL, Aug. 22–27, 1993.

Wei et al, *J. Med. Chem.,* 36, 249–255 (1993).

Hoffman et al, *J. Med. Chem.,* 35, 3784–3791 (1992).

Saari et al, *J. Med. Chem.,* 35, 3792–3802 (1992).

Romero et al, *J. Med. Chem.,* 36, 1505–1508 (1993).

Hargrave, *J. Med. Chem.,* 34, 2231–2241 (1991).

Merluzzi, *Science,* 250, 1411–1413 (1990).

Williams et al, *J. Med. Chem.,* 36, 1291–1294 (1993).

Hsu et al, *Proc. Natl. Acad. Sci. USA,* 909, 6395–6399 (1993).

S.J. Fittkau, *J. Prakt. Chem.,* 315, 1037 (1973).

Parikh et al., *J. Am. Chem. Soc.,* 89, 5505 (1967).

Reetz et al, *Angew Chem. Int. Ed. Engl.,* 26, 1141 (1987).

Miller et al, *Science,* 246, 1149 (1989).

Meek et al, *Nature,* 343, (1990).

T.J. McQuade et al, *Science,* 247, 454–456 (1989).

Rich et al, *Peptide Inhibitors of Proteases,* 511–520, 1987.

Pearle, et al, Nature, 328, 482 (1987).

Fletcher, Pharmacotherapy, 13(6), 627–33 (1993).

Perno et al, J. Infect. Disease, 168:1148–1156 (1993).

Yarcham et al, J. Infect. Disease, 169:9–17 (1994).

RETROVIRAL PROTEASE INHIBITOR COMBINATIONS

This is a continuation of application Ser. No. 08/253,638 filed Jun. 3, 1984 (now abandoned).

BACKGROUND OF THE INVENTION

1. Field of the Invention

The present invention relates to a method for the treatment of mammalian retrovirus infections, such as human immunodeficiency virus (HIV), using combinations of retroviral protease inhibitors which are effective in preventing the replication of mammalian retroviruses, like HIV, in vitro and in vivo. This invention, in particular, relates to protease inhibitor compounds used in combination therapy with other protease inhibitor compounds.

2. Related Art

During the replication cycle of retroviruses, gag and gag-pol gene transcription products are translated as proteins. The proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease active site that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit specific processing of structural proteins and the release of retroviral protease itself. In this manner, retroviral replication proteases can be effectively inhibited.

Several classes of mimetic compounds have been proposed, particularly for inhibition of proteases, such as for inhibition of HIV protease. Such mimetics include hydroxyethylamine isosteres, reduced amide isosteres and non-peptide isosteres. See for example, EP 0 346 847; EP 0 342 541; Roberts et al, "Rational Design of Peptide-Based Proteinase Inhibitors," Science, 248, 358 (1990); Erickson et al, "Design Activity, and 2.8 Å Crystal Structure of a $C_2$ Symmetric Inhibitor Complexed to HIV-1 Protease," Science, 249, 527 (1990); and S. Thaisrivongs, "Structure-Based Design of Non-Peptide HIV Protease Inhibitors," 35th Annual Buffalo Medicinal Chemistry Meeting, State University of New York at Buffalo, Buffalo, N.Y., May 22–25, 1994.

A problem for retroviral protease inhibitors, like HIV protease inhibitors, has been the development of strains of the virus resistant to the inhibitor. For example, Merck & Co.'s HIV protease inhibitor L-735,524 is effective against HIV infections in humans, but L-735,524 resistant strains of HIV later develop in patients (Waldholz, The Wall Street Journal, Feb. 25, 1994, page B3; and Condra et al., Nature 374:569–571 (1995)). Other examples can be found in Vacca et al., Proc. Natl. Acad. Sci. USA 91:4096–4100 (1994); Ho et al., J. Virol. 68:2016–2020 (1994); and Sardana et al., Biochem. 33:2004–2010 (1994).

BRIEF DESCRIPTION OF THE INVENTION

The present invention is directed to a method for the treatment of mammalian retrovirus infections, such as human immunodeficiency virus (HIV), using combinations of retroviral protease inhibitors which are effective in preventing the replication of the retroviruses in vitro or in vivo. This invention, in particular, relates to protease inhibitor compounds used in combination therapy with other protease inhibitor compounds. Further, this combination may also be used in combination with other anti-viral agents.

DETAILED DESCRIPTION OF THE INVENTION

Retroviral protease is a critical enzyme in the retroviral replication process. Propagation of a retrovirus, such as HIV, can be impeded by exposing the virus to a retroviral protease inhibitor. However, with prolonged exposure of the retrovirus to the protease inhibitor, the variant retroviruses can be selected such that a new predominant strain of retrovirus resistant to the protease inhibitor emerges. The new predominant strain of retrovirus can produce a protease which is no longer inhibited or more frequently is insufficiently inhibited by the protease inhibitor and can freely propagate even in the presence of the protease inhibitor unless the concentration of the inhibitor is substantially increased. The present invention provides a method for overcoming the development of retroviral strains which are resistant to a retroviral protease inhibitor.

The present method provides for the administration to a mammal, such as a human, monkey, cat and the like, of an effective amount of at least two retroviral protease inhibitors. The administration may be accomplished by co-administration of at least two retroviral protease inhibitors, i.e., administering two or more retroviral protease inhibitors such that an effective amount of at least two inhibitors are present in said mammal at any one time. Alternatively, the administration may be accomplished by sequential or alternating administration of at least two retroviral protease inhibitors, i.e. administering two or more retroviral protease inhibitors such that an effective amount of only one inhibitor is present in said mammal at any one time. With the proper selection of the retroviral protease inhibitors, this method can effectively control the propagation of the retrovirus even in the presence of resistant strains to any one of the inhibitors.

The retroviral protease inhibitors are selected based on the profile of resistant strain(s) of the retrovirus which emerge in vivo or in vitro upon exposure of the inhibitor to a propagating culture of the retroviruses. The retroviral protease inhibitors are selected for lack of cross-resistance by at least one retroviral resistant strain. A retroviral strain is considered to be cross-resistant to two protease inhibitors when the retroviral strain is resistant to both inhibitors. While some cross-resistance can be tolerated, preferably, no cross-resistance exists between the selected retroviral protease inhibitors when taken as a group. Thus a variant (or mutant strain) of retrovirus which may develop as a result of exposure to a first retroviral protease inhibitor would still be inhibited by a second retroviral protease inhibitor or which may develop as a result of exposure to both a first and second retroviral protease inhibitors would still be inhibited by a third retroviral protease inhibitor or a fourth retroviral protease inhibitor and so forth.

A comparison of cross-resistance profiles between various protease inhibitors are made and compounds are selected for combination therapy that preferably exhibit little or no cross-resistance. The drug resistance phenotype may be divided into no resistance, low level resistance (less than about 10 fold shift in $EC_{50}$ or $EC_{90}$), intermediate level resistance (about 10 to about 100 fold shift in $EC_{50}$ or $EC_{90}$) or high level resistance (greater than about 100 fold shift in $EC_{50}$ or $EC_{90}$). It is anticipated that drug resistance will correlate with a reduced effect on patient viral load when the achievable in vivo inhibitor concentrations have a reduced protease inhibition effect on the resistant virus. Thus the more preferred combinations of protease inhibitors will be those that exhibit minimal cross-resistance profiles (i.e., preferably, not more than intermediate level resistance; more preferably, not more than low level resistance; and most preferably, no resistance) and maximal intrinsic potency for wild-type and/or resistant viruses selected against another inhibitor. For example, preferred compounds for use in combination with a first compound will preferably be effective against strains of virus which are intermediate level, more preferably high level, resistant to the first compound. The pharmacology and toxicology of each inhibitor and combination are also factors in the selection of inhibitors for combination therapy.

More preferably, retroviral protease inhibitors are chosen when at least one viral resistant strain to a first retroviral protease inhibitor and at least one viral resistant strain to a second retroviral protease inhibitor having different amino acid substitutions in the protease peptide sequence that affect the same substrate binding site region of the protease and contributes to the observed inhibitor resistance. Thus the number of possible amino acid substitutions that may occur in the same site in the protease are limited. This is particularly true when the site is critical to activity, effectiveness and/or stability of the enzyme.

This event was observed in relation to the HIV protease inhibitors of Examples 1 and 2 hereof. Retroviral resistance to the compound of Example 1 resulted from site mutation at amino acid 88 of HIV protease (substitution of asparagine 88 with aspartic acid 88). Retroviral resistance to the compound of Example 2 also resulted from site mutation at amino acid 88 of HIV protease (substitution of asparagine 88 with serine 88). Some substitutions at amino acid 88 are known to cause loss of enzyme activity (Loeb et al., Nature 340:387–400 (1989)). Thus the administration of both HIV protease inhibitors of Examples 1 and 2 substantially reduces the likelihood of further successful production of a resistant strain of virus cross-resistant to both inhibitors. No resistance to both inhibitors used in combination has been detected through 6 weeks of treatment compared to the emergence of a resistant phenotype to a single inhibitor in the same time frame. In addition to site mutations which affect enzyme activity, other site mutations in the same variant may also arise which do not substantially affect enzyme activity and/or resistance.

Alternatively, more preferably, retroviral protease inhibitors are selected when at least one viral resistant strain to a first retroviral protease inhibitor has an increased sensitivity to said second protease inhibitor or when at least one viral resistant strain to a second retroviral protease inhibitor has an increased sensitivity to said first protease inhibitor.

Representative retroviral protease inhibitors which are suitable for use in the present method include, but are not limited to, the protease inhibitors disclosed and described in co-owned and co-pending U.S. patent applications Ser. Nos. 08/152,934 (filed Nov. 15, 1993), 08/253,531 (filed Jun. 3, 1994), 08/109,787 (filed Aug. 20, 1993), 08/110,911 (filed Aug. 24, 1993), 08/110,913 (filed Aug. 24, 1993, 08/110,912 (filed Aug. 24, 1993), 08/204,827 (filed Mar. 2, 1994), 07/886,556 (filed May 20, 1992), 07/886,663 (filed May 20, 1992), 07/886,531 (filed May 20, 1992), 08/148,817 (filed Nov. 8, 1993), 08/886,700 (filed May 21, 1992) and 07/998, 187 (filed Dec. 29, 1992) and PCT Patent Applications Nos. PCT/US93/10552 (filed Oct. 29, 1993), PCT/US93/10460 (filed Oct. 29, 1993) and PCT/US93/10461 (filed Oct. 29, 1993), each of which are incorporated herein by reference in their entirety. Additional retroviral protease inhibitors which are suitable for use in the present method include, but are not limited to, the protease inhibitors disclosed and described in U.S. Pat. 5,157,041; EP 346,847; U.S. patent application Ser. No. 07/883,825 (filed May 15, 1992); WO 93/09096; Tet. Lett. 35:673–676 (1994); Proc. Natl. Acad. Sci. USA, 91: 4096–4100 (1994); Y. N. Wong et al., Biopharm. & Drug Dispos. 15:535–544 (1994); M. L. West and D. P. Fairlie, Trends Pharmacol. Sci. 16:67–75 (1995); and S. Thaisrivongs, "HIV Protease Inhibitors", Ann. Reports Med. Chem., Vol. 29, Chap. 14, pp. 133–144 (1994) (Academic Press, J. Bristol, Ed.), each of which is incorporated herein by reference in their entirety.

Without further elaboration, it is believed that one skilled in the art can, using the preceding description, utilize the present invention to its fullest extent. The following preferred specific embodiments are not intended to provide an exhaustive description of all possible compound combinations but merely to provide examples of drug combinations that are anticipated to be effective. Similar testing of these and other protease inhibitors using resistant viral isolates, not limited to those listed below, can help identify suitable drug combinations. Therefore, the following preferred specific embodiments are to be construed as merely illustrative, and not limitative of the remainder of the disclosure in any way whatsoever.

EXAMPLE 1

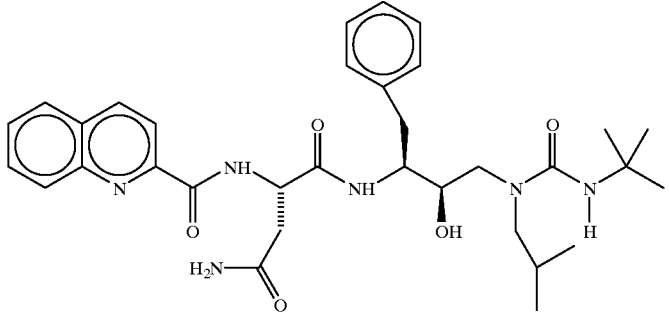

[1S-[1R*(R*),2S*]]-N$^1$-[3-[[[(1,1-dimethylethyl)amino] carbonyl])2-methylpropyl)amino]-2-hydroxy-1-(phenylmethyl)propyl]-2-[(2-quinolinylcarbonyl)amino]-butanediamide can be prepared according to the methods disclosed in co-owned and co-pending U.S. patent applications Ser. Nos. 08/152,934 (filed Nov. 15, 1993) and 08/156, 498 (filed Nov. 23, 1993), both incorporated herein by reference in their entirety.

EXAMPLE 2

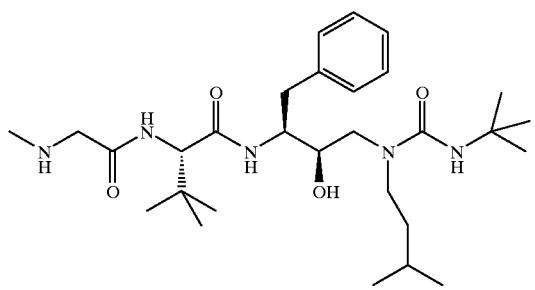

(2R,3S)-3-(N-methylaminoacetyl-L-tert-butylglycinyl)amino-1-(N-isoamyl-N-(tert-butylcarbamoyl))amino-4-phenyl-2-butanol can be prepared according to the methods disclosed in co-owned and co-pending U.S. patent applications Ser. Nos. 08/109,787 (filed Aug. 20, 1993 ), Attorney docket No. 2766/1 co-filed with the present application, and 08/156,498 (filed Nov. 23, 1993, all three incorporated herein by reference in their entirety.

EXAMPLE 3

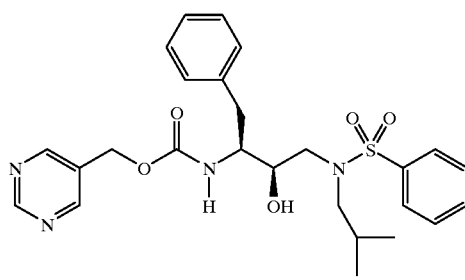

[2R-hydroxy-3-[[(4-methoxyphenyl)sulfonyl](2-methylpropyl)amino]-1S-(phenylmethyl)propyl]carbamic acid 5-pyrimidylmethyl ester can be prepared according to the methods disclosed in co-owned and co-pending U.S. patent applications Ser. Nos. 08/110,911 (filed Aug. 24, 1993) and 08/156,498 (filed Nov. 23, 1993), both incorporated herein by reference in their entirety.

EXAMPLE 4

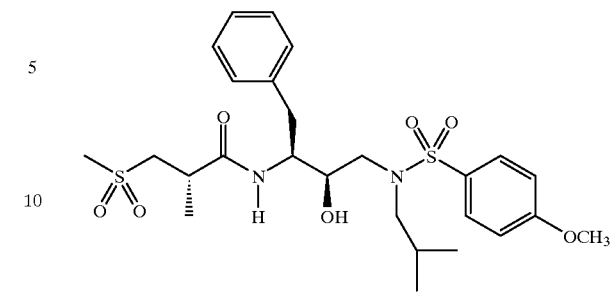

[1S-[1R*(R*),2S*]]-N-[2-hydroxy-3-[$N^1$-(2-methylpropyl)-$N^1$-(4-methoxyphenylsulfonyl)amino]-1-(phenylmethyl)propyl]-2-methyl-3-(methylsulfonyl)propanamide can be prepared according to the methods disclosed in co-owned and co-pending U.S. patent applications Ser. Nos. 08/110,913 (filed Aug. 24, 1993) and 08/156,498 (filed Nov. 23, 1993), both incorporated herein by reference in their entirety.

EXAMPLE 5

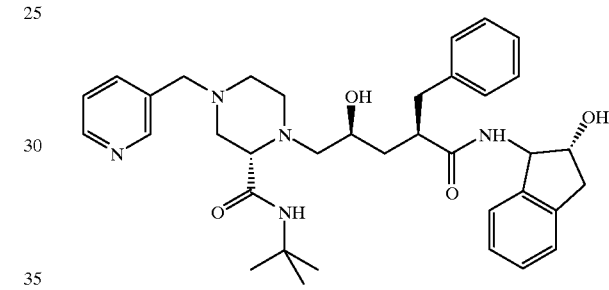

N-(2(R)-Hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (L-735,524) can be prepared according to the methods disclosed in U.S. patent application Ser. No. 07/883,825 (filed May 15, 1992), WO 93/09096, Tet. Lett. 35:673–676 (1994) and Proc. Natl. Acad. Sci. USA, 91:4096–4100 (1994), each of which is incorporated herein by reference in its entirety.

EXAMPLE 6

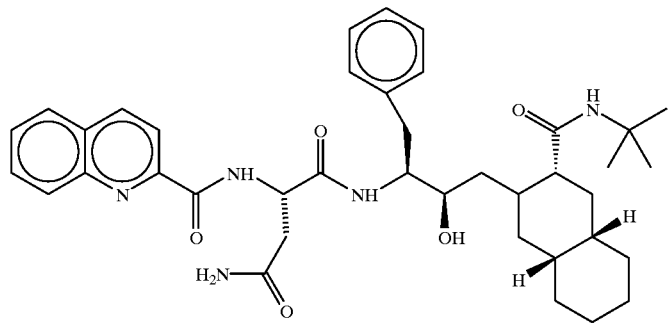

N-tert-Butyl decahydro-2-[2 (R) -hydroxy-4-phenyl-3(S)-[[N-(2-quinolylcarbonyl)-L-asparaginyl]amino]butyl]-(4aR,8aS)-isoquinoline-3(S)-carboxamide (Ro 31-8959) can be prepared according to the methods disclosed in U.S. Pat. No. 5,157,041, incorporated herein by reference in its entirety.

EXAMPLE 7

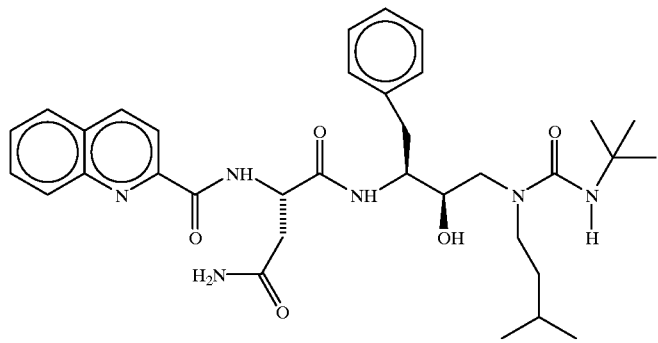

[1S-[1R*(R*),2S*]]-$N^1$-[3-[[[(1,1-dimethylethyl) amino]carbonyl](3-methylbutyl)amino]-2-hydroxy-1-(phenylmethyl)propyl]-2-[(2-quinolinylcarbonyl)amino]-butanediamide can be prepared according to the methods disclosed in co-owned and co-pending U.S. patent applications Ser. Nos. 08/152,934 (filed Nov. 15, 1993) and 08/156,498 (filed Nov. 23, 1993), both incorporated herein by reference in their entirety.

EXAMPLE 8

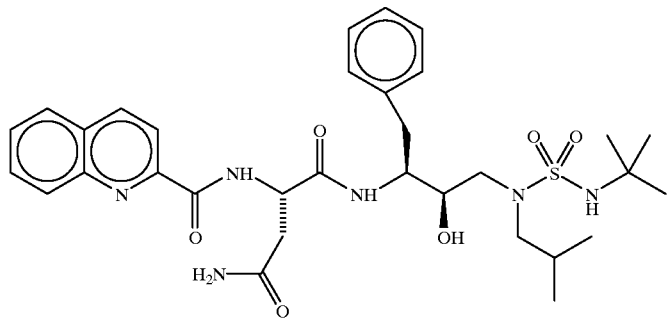

N-[3-[$N^2$-[$N^1$-(1,1-dimethylethyl)aminosulfonyl]-$N^2$-(2-methylpropyl)amino]-2R-hydroxy-1S-(phenylmethyl)propyl]-2S-[(2-quinolinylcarbonyl)amino]butanediamide can be prepared according to the methods disclosed in co-owned and co-pending PCT Patent Application No. PCT/US93/10552 (filed Oct. 29, 1993) and U.S. patent application Ser. No. 08/156,498 (filed Nov. 23, 1993), both incorporated herein by reference in their entirety.

EXAMPLE 9

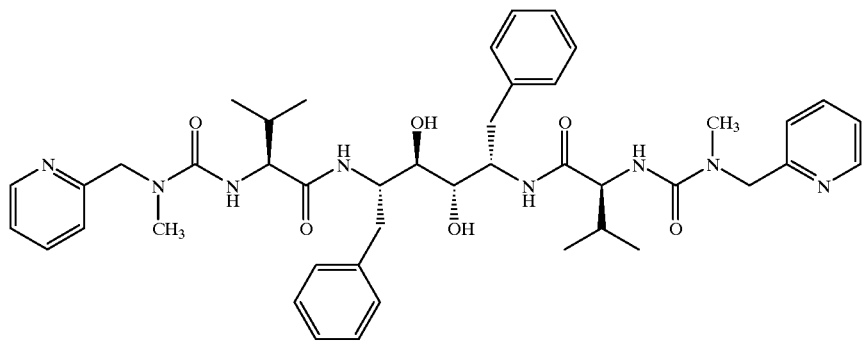

(2S,3R,4S,5S)-2,5-Bis-[N-[N-[[N-methyl-N-(2-pyridinylmethyl)amino]carbonyl]valinyl]amino]-3,4-dihydroxy-1,6-diphenylhexane (A-77003) can be prepared according to the methods disclosed in J. Med. Chem. 36:320–330 (1993), which is incorporated herein by reference in its entirety.

EXAMPLE 10

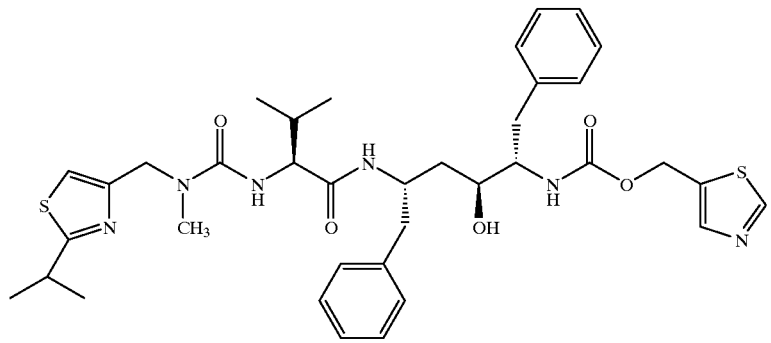

(2S,3S,5S)-5-[N-[N-[N-methyl-N-[(2-isopropyl-4-thiazolyl)methyl]amino]carbonyl]valinyl]amino]-2-[N-[(5-thiazolyl)methoxycarbonyl]amino]-3-hydroxy-1,6-diphenylhexane (A-84538, ABT-538) can be prepared according No. WO 94/14436 (filed Dec. 16, 1993), which is incorporated herein by reference in its entirety.

EXAMPLE 11

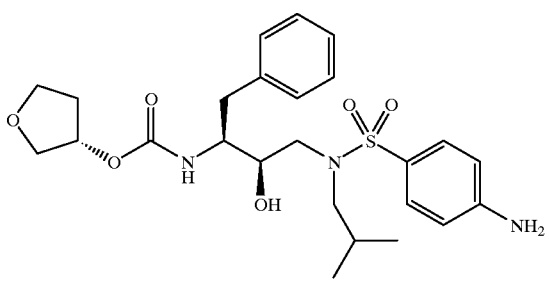

[2R-hydroxy-3-[[(4-aminophenyl)sulfonyl](2-methylpropyl)amino]-1S-(phenylmethyl)propyl]carbamic acid 3S-tetrahydrofuranyl ester (VX-478) can be prepared according to the methods disclosed in PCT Patent Applications Ser. No. WO 94/05639 (filed Sep. 7, 1993), incorporated herein by reference in its entirety.

EXAMPLE 12

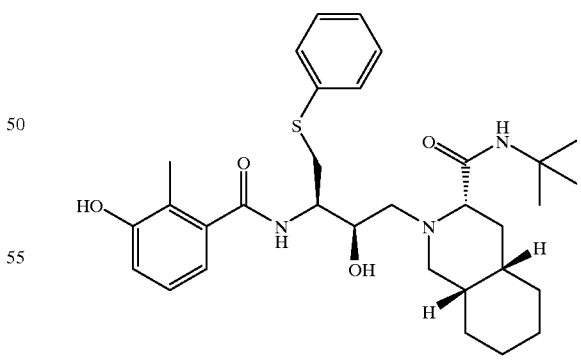

N-tert-Butyl decahydro-2-[2(R)-hydroxy-4-(phenylthio)-3(S)-[[N-[(2-methyl-3-hydroxyphenyl)carbonyl]amino]butyl](4aR,8aS)-isoquinoline-3(S)-carboxamide (AG-1343, AG-1350) can be prepared according to the methods disclosed in Bioorg. & Med. Chem. Let. 5:715–720, 5:721–726 and 5:727–732 (1995), each of which is incorporated herein by reference in their entirety. In particular, the HOBT active ester of 3-hydroxy-2-methylbenzoic acid (Bioorg. & Med. Chem. Let. 5:727–732 (1995)) can be coupled to N-tert-Butyl decahydro-2-[2(R)-hydroxy-4-(phenylthio)-3(S)-aminobutyl]-(4aR,8aS)-isoquinoline-3(S)-carboxamide (Bioorg. & Med. Chem. Let. 5:715–720 (1995)).

EXAMPLE 13

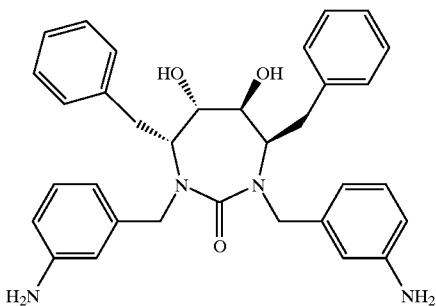

[4R-(4α,5α,6β,7β)]-1,3-bis[(3-aminophenyl)methyl] hexahydro-5,6-dihydroxy-4,7-bis(phenylmethyl)-2H-1,3-diazepin-2-one (DMP-450, XM-412) can be prepared according to the methods disclosed in PCT Patent Application WO 93/07128, incorporated herein by reference in its entirety. In particular, 3-nitrophenylmethyl halide, such as 3-nitrophenylmethylchloride or bromide, is reacted with the hydroxy protected derivative of [4R-(4α5α,6β,7β)]-hexahydro-5,6-dihydroxy-4,7-bis(phenylmethyl)-2H-1,3-diazepin-2-one followed by deprotection of the hydroxy groups (see WO 93/07128) and reduction of the nitro groups to the amino groups. Such reductions can be accomplished using standard procedures well known to those skilled in the art.

EXAMPLE 14

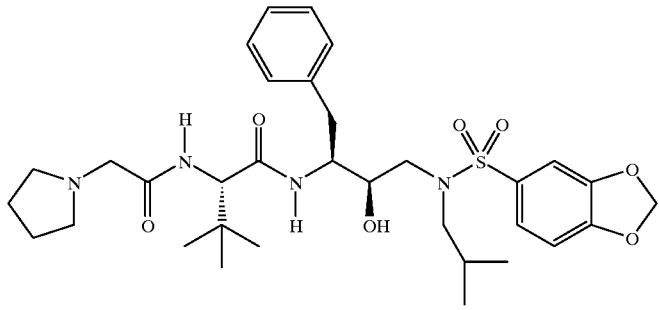

Preparation of N-[2R-hydroxy-3-[[(1,3-benzodioxol-5-yl)sulfonyl](2-methylpropyl)amino]-1S-(phenylmethyl)propyl]-2S-[[(pyrrolidin-1-yl)acetyl]amino]-3,3-dimethylbutanamide Part A: Preparation of 1,3-benzodioxole-5-sulfonyl chloride To a solution of 4.25 g of anhydrous N,N-dimethylformamide at 0° C. under nitrogen was added 7.84 g of sulfuryl chloride, whereupon a solid formed. After stirring for 15 minutes, 6.45 g of 1,3-benzodioxole was added, and the mixture heated at 100° C. for 2 hours. The reaction was cooled, poured into ice water, extracted with methylene chloride, dried over magnesium sulfate, filtered and concentrated to give 7.32 g of crude material as a black oil. This was chromatographed on silica gel using 20% methylene chloride/hexane to afford 1.9 g of (1,3-benzodioxol-5-yl)sulfonyl chloride.

Alternatively, to a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,3-Benzodioxole (1905 g, 15.6 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate which kept the temperature below 20° C. After the addition of water was complete, the mixture was stirred for 10 minutes. The layers were separated and the organic layer was washed again twice with water (5l). The organic layer was dried with magnesium sulfate (500 g) and filtered to remove the drying agent. The solvent was removed under vacuum at 50° C. The resulting warm liquid was allowed to cool at which time a solid began to form. After one hour, the solid was washed with hexane (400 mL), filtered and dried to provide the desired sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

Part B: Preparation of 2S-[Bis(phenylmethyl)amino]-3-phenylpropanol

METHOD 1: 2S-[Bis(phenylmethyl)amino]-3-phenylpropanol from the DIBAL Reduction of N,N-bis(phenylmethyl)-L-Phenylalanine phenylmethyl ester Step 1: A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time ~25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. N,N-bis(phenylmethyl)-L-phenylalanine phenylmethyl ester can be purified by column chromatography (silica gel, 15% ethyl acetate/hexane). Usually the product is pure enough to be used directly in the next step without further purification. EIMS: m/z 434 (M-1).

Step 2: The benzylated phenylalanine phenylmethyl ester (0.302 mol) from the previous reaction was dissolved in toluene (750 mL) and cooled to −55° C. A 1.5M solution of DIBAL in toluene (443.9 mL, 0.666 mol) was added at a rate to maintain the temperature between −55 to −50° C. (addition time−1 hr). The mixture was stirred for 20 minutes under a nitrogen atmosphere and then quenched at −55° C. by the slow addition of methanol (37 ml). The cold solution was then poured into cold (5° C.) 1.5N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of 2S-[Bis(phenylmethyl)amino]-3-phenylpropanol, 40% yield from L-phenylalanine. Anal. Calcd. for $C_{23}H_{25}ON$: C, 83.34; H, 7.60; N, 4.23. Found: C, 83.43; H, 7.59; N, 4.22.

METHOD 2: Preparation of βS-2-[Bis(phenylmethyl)amino]benzene-propanol from the N,N-Dibenzylation of L-Phenylalaninol L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was recrystallized from 1.1 L of ethyl acetate/heptane (1:10). The product was isolated by filtration (at −8° C.), washed with 1.6 L of cold (−10° C.) ethyl acetate/heptane (1:10) and air-dried to give 339 g (88% yield) of 2S-[Bis(phenylmethyl)amino]-3-phenylpropanol, Mp=71.5–73.0° C.

Part C: Preparation of 2S-[Bis(phenylmethyl)amino]-3-phenylpropanaldehyde

METHOD 1: 2S-[Bis(phenylmethyl)amino]-3-phenylpropanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. The solution was stirred at ambient temperature under a nitrogen atmosphere for 1.5 hour. The reaction mixture was cooled with ice water and quenched with 1.6 L of cold water (10–15° C.) over 45 minutes. The resultant solution was extracted with ethyl acetate (2.0 L), washed with 5% citric acid (2.0 L) and brine (2.2 L), dried over $MgSO_4$ (280 g) and filtered. The solvent was removed in vacuo and then dried under vacuum to give 198.8 g of 2S-[Bis-(phenylmethyl)amino]-3-phenylpropanaldehyde as a pale yellow oil (99.9%). The crude product obtained was pure enough to be used directly in the next step without purification.

METHOD 2: A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time −1.25 hr). The mixture was stirred for 5 min. followed by addition of a solution of 2S-[bis(phenylmethyl)amino]-3-phenylpropanol (0.074 mol) in 100 ml of dichloromethane (addition time −20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give 2S-[bis(phenylmethyl)amino]-3-phenylpropanaldehyde. The aldehyde was carried on to the next step without purification.

METHOD 3: To a mixture of 1.0 g (3.0 mmoles) of 2S-[bis(phenylmethyl)amino]-3-phenylpropanol 0.531 g (4.53 mmoles) of N-methylmorpholine, 2.27 g of molecular sieves (4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of 2S-[bis(phenylmethyl)amino]-3-phenylpropanaldehyde as a pale yellow oil.

METHOD 4: To a solution of 1.0 g (3.02 mmoles) of 2S-[bis(phenylmethyl)amino]-3-phenylpropanol in 9.0 mL of toluene was added 4.69 mg (0.03 mmoles) of 2,2,6,6-tetramethyl-1-piperidinyloxy, free radical (TEMPO), 0.32 g(3.11 mmoles) of sodium bromide, 9.0 mL of ethyl acetate and 1.5 mL of water. The mixture was cooled to 0° C. and an aqueous solution of 2.87 mL of 5% household bleach containing 0.735 g (8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The aqueous layer was extracted twice with 20 mL of ethyl acetate. The combined organic layer was washed with 4.0 mL of a solution containing 25 mg of potassium iodide and water (4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, 2S-[bis(phenylmethyl)amino]-3-phenyl propanaldehyde.

Part D: Preparation of N,N-dibenzyl-3(S)-amino-1,2-(S)-epoxy-4-phenylbutane

METHOD 1: A solution of 2S-[Bis(phenylmethyl)amino]-3-phenylpropanaldehyde (191.7 g, 0.58 mol) and chloroiodomethane (56.4 mL, 0.77 mol) in tetrahydrofuran (1.8 L) was cooled to −30 to −35° C. in a stainless steel reactor under a nitrogen atmosphere. A solution of n-butyl lithium in hexane (1.6M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyl lithium (110 mL) at <-25° C. After addition the mixture was stirred at -30 to -35° C. for 10 minutes. This was repeated once. (2) Additional chloroiodomethane (8.5 mL, 0.11 mol) was added, followed by n-butyl lithium (55 mL, 0.088 mol) at <-25° C. After addition the mixture was stirred at -30 to -35° C. for 10 minutes. This was repeated 5 times. (3) Additional chloroiodomethane (8.5 mL, 0.11 mol) was added, followed by n-butyl lithium (37 mL, 0.059 mol) at <-25° C. After addition the mixture was stirred at -30 to -35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10°C. and quenched with 1452 g of 16% ammonium chloride solution, keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated in vacuo. The brown oil residue was dried at 70° C. in vacuo (0.8 bar) for 1 hour to give 222.8 g of crude material. The crude product is usually used directly in the next step without purification.

METHOD 2: A solution of the crude aldehyde 0.074 mol and chloroiodomethane (7.0 ml, 0.096 mol) in tetrahydrofuran (285 ml) was cooled to -78° C., under a nitrogen atmosphere. A 1.6M solution of n-butyl lithium in hexane (25 ml, 0.040 mol) was then added at a rate to maintain the temperature at -75° C. After the first addition, additional chloroiodomethane (1.6 ml, 0.022 mol) was added again, followed by n-butyl lithium (23 ml, 0.037 mol), keeping the temperature at -75° C. The mixture was stirred for 15 min. Each of the reagents, chloroiodomethane (0.70 ml, 0.010 mol) and n-butyl lithium (5 ml, 0.008 mol) were added 4 more times over 45 min. at -75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification.

METHOD 3: A solution of 2S-[Bis(phenylmethyl) amino]-3-phenylpropanaldehyde (178.84 g, 0.54 mol) and bromochloromethane (46 mL, 0.71 mol) in tetrahydrofuran (1.8 L) was cooled to -30 to -35° C. in a stainless steel reactor under a nitrogen atmosphere. A solution of n-butyl lithium in hexane (1.6M, 340 mL, 0.54 mol) was then added at a rate that maintained the temperature below -25° C. After addition the mixture was stirred at -30 to -35° C. for 10 minutes. More additions of reagents were carried out in the following manner: (1) additional bromochloromethane (14 mL) was added, followed by n-butyl lithium (102 mL) at <-25° C. After addition the mixture was stirred at -30 to -35° C. for 10 minutes. This was repeated once. (2) Additional bromochloromethane (7 mL, 0.11 mol) was added, followed by n-butyl lithium (51 mL, 0.082 mol) at <-25° C. After addition the mixture was stirred at -30 to -35° C. for 10 minutes. This was repeated 5 times. (3) Additional bromochloromethane (7 mL, 0.11 mol) was added, followed by n-butyl lithium (51 mL, 0.082 mol) at <-25° C. After addition the mixture was stirred at -30 to -35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution, keeping the temperature below 23° C. The mixture was stirred for 10 minutes and the organic and aqueous layers were separated. The aqueous phase was extracted with ethyl acetate (2–500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 hour to give 222.8 g of crude material.

Part E: Preparation of N-[3(S)-[N,N-bis(phenylmethyl) amino]-2(R)-hydroxy-4-phenylbutyl]-N-isobutylamine-oxalic acid salt Step 1: To a solution of crude N,N-dibenzyl-3(S)-amino-1,2(S)-epoxy-4-phenylbutane (388.5 g, 1.13 mol) in isopropanol (2.7 L) (or ethyl acetate) was added isobutylamine (1.7 kgm, 23.1 mol) over 2 min. The temperature increased from 25° C. and to 30° C. The solution was heated to 82° C. and stirred at this temperature for 1.5 hours. The warm solution was concentrated in vacuo. The brown oil residue was dried in vacuo (0.8 mm Hg) for 16 h to give 450 g of product as a crude oil.

Step 2: To a solution of oxalic acid (8.08 g, 89.72 mmol) in methanol (76 mL) was added a solution of crude 3(S)-[N,N-bis(phenylmethyl)amino]-1-(2-methylpropyl)amino-4-phenylbutan-2(R)-ol in ethyl acetate (90 mL) over 15 minutes. The mixture was stirred at room temperature for about 2 hours. Solid was isolated by filtration, washed with ethyl acetate (2×20 mL) and dried in vacuo for about 1 hour to yield 21.86 g of 97% diastereomerically pure salt. Mp=174.99° C.; Microanalysis: Calc.: C 71.05%, H 7.50%, N 5.53%; Found: C 71.71%, H 7.75%, N 5.39%.

Alternatively, crude 3(S)-[N,N-bis(phenylmethyl) amino]-1-(2-methylpropyl)amino-4-phenylbutan-2(R)-ol (5 g) was dissolved in methyl-tert-butylether (MTBE) (10 mL) and oxalic acid (1 g) in methanol (4 mL) was added. The mixture was stirred for about 2 hours. The resulting solid was filtered, washed with cold MTBE and dried to yield 2.1 g of white solid of about 98.9% diastereomerically pure (based on HPLC peak areas).

Part F: Preparation of 1-[N-[(1,3-benzodioxol-5-yl) sulfonyl]-N-(2-methylpropyl)amino]-3(S)-[N,N-bis (phenylmethyl)amino]-4-phenyl-2(R)-butanol To N-[3(S)-[N,N-bis(phenylmethyl)amino]-2(R)-hydroxy-4-phenylbutyl]-N-isobutylamine-oxalic acid salt (354.7 g, 0.7 mole) in 1,4-dioxane (2000 mL) was added a solution of potassium carbonate (241.9 g, 1.75 moles) in water (250 mL). The mixture was stirred for 2 hours at room temperature followed by addition of 1,3-benzodioxole-5-sulfonyl chloride (162.2 g, 0.735 mole) in 1,4-dioxane (250 mL) over 15 minutes. The reaction mixture was stirred at room temperature for 18 hours. Ethyl acetate (1000 mL) and water (500 mL) were added and stirring continued for another 1 hour. The aqueous layer was separated and further extracted with ethyl acetate (200 mL). The combined ethyl acetate layers were washed with 25% brine solution (500 mL) and dried over anhydrous magnesium sulfate. After filtering and washing the magnesium sulfate with ethyl acetate (200 mL), the solvent was removed in vacuo to yield the desired sulfonamide as an viscous yellow foamy oil (440.2 g 105% yield). HPLC/MS (electrospray) (m/z 601 [M+H]$^+$).

Alternatively, N-[3(S)-[N,N-bis(phenylmethyl)amino]-2 (R)-hydroxy-4-phenylbutyl]-N-isobutylamine-oxalic acid salt (2800 g, 5.53 moles) and THF (4 L) were added to a 22 L round bottom flask fitted with a mechanical stirrer. Potassium carbonate (1921 g, 13.9 moles) was dissolved in water (2.8 L) and added to the THF slurry. The mixture was then stirred for one hour. 1,3-benzodioxole-5-sulfonyl chloride (1281 g, 5.8 moles) was dissolved in THF (1.4 L) and added to the reaction mixture over 25 minutes. An additional 200 mL of THF was used to rinse the addition funnel. The reaction was allowed to stir for 14 hours and then water (4 L) was added. This mixture was stirred for 30 minutes and the layers allowed to separate. The layers was removed and the aqueous layer washed twice with THF (500 mL). The combined THF layers were dried with magnesium sulfate (500 g) for one hour. This solution was then filtered to remove the drying agent and used in subsequent reactions.

Part G: Preparation of 1-[N-[(1,3-benzodioxol-5-yl)sulfonyl]-N-(2-methylpropyl)amino]-3(S)-amino-4-phenyl-2(R)-butanol-methanesulfonic acid salt Crude 1-[N-[(1,3-benzodioxol-5-yl)sulfonyl]-N-(2-methylpropyl)amino]-3(S)-[bis(phenylmethyl)amino]-4-phenyl-2(R)-butanol (6.2 g, 0.010 moles) was dissolved in methanol (40 mL). Methanesulfonic acid (0.969 g, 0.010 moles) and water (5 mL) were then added to the solution. The mixture was placed in a 500 mL Parr hydrogenation bottle containing 20% Pd(OH)$_2$ on carbon (255 mg, 50% water content). The bottle was placed in the hydrogenator and purged 5 times with nitrogen and 5 times with hydrogen. The reaction was allowed to proceed at 35° C. with 63 PSI hydrogen pressure for 18 hours. Additional catalyst (125 mg) was added and, after purging, the hydrogenation continued for and additional 20 hours. The mixture was filtered through celite which was washed with methanol (2×10 mL). Approximately one third of the methanol was removed under reduced pressure. The remaining methanol was removed by aziotropic distillation with toluene at 80 torr. Toluene was added in 15, 10, 10 and 10 mL portions. The product crystallized from the mixture and was filtered and washed twice with 10 mL portions of toluene. The solid was dried at room temperature at 1 torr for 6 hours to yield the amine salt (4.5 g, 84%): m/z 421 [M+H]$^+$.

Alternatively, to a THF solution of crude 1-[N-[(1,3-benzodioxol-5-yl)sulfonyl]-N-(2-methylpropyl)amino]-3(S)-[bis(phenylmethyl)amino]-4-phenyl-2(R)-butanol was added water (500 mL) followed by methanesulfonic acid (531 g, 5.5 moles). The solution was stirred to insure complete mixing and added to a 5 gallon autoclave. Pearlman's catalyst (200 g of 20% Pd(OH)$_2$ on C/50% water) was added to the autoclave with the aid of THF (500 mL). The reactor was purged four times with nitrogen and four times with hydrogen. The reactor was charged with 60 psig of hydrogen and stirring at 450 rpm started. After 16 hours, HPLC analysis indicated that a small amount of the mono-benzyl intermediate was still present. Additional catalyst (50 g) was added and the reaction was allowed to run overnight. The solution was then filtered through celite (500 g) to remove the catalyst and concentrated under vacuum in five portions. To each portion, toluene (500 mL) was added and removed under vacuum to azeotropically removed residual water. The resulting solid was divided into three portions and each washed with methyl t-butyl ether (2 L) and filtered. The residual solvent was removed at room temperature in a vacuum oven at less than 1 torr to yield the 2714 g of the expected salt.

Part H: Preparation of N-[2R-hydroxy-3-[[(1,3-benzodioxol-5-yl)sulfonyl](2-methylpropyl)amino]-1S-(phenylmethyl) propyl]-2S-[(phenylmethoxycarbonyl)amino]-3,3-dimethylbutanamide To a solution of 118.8 g (0.776 mol) of N-hydroxybenzotriazole and 137.1 g (0.52 mol) of N-carbobenzyloxycarbonyl-L-tert-leucine in 750 mL of anhydrous DMF at 0° C. under a nitrogen atmosphere, was added 109.1 g (0.57 mol) of EDC. After stirring at 0° C. for 2 hours, a solution of 273 g (0.53 mol) of 2R-hydroxy-3-[[(1,3-benzodioxol-5-yl)sulfonyl](2-methylpropyl)amino]-1S-(phenylmethyl)propylamine methanesulfonate, previously neutralized with 228 mL (210 g, 2.08 mol) of 4-methylmorpholine, in 250 mL of anhydrous DMF was added. After stirring at 0° C. for 30 minutes, the mixture stirred at room temperature for 18 hours. The solvents were removed under reduced pressure at 45° C., 1.5 L of ethyl acetate added, washed with 5% citric acid, saturated sodium bicabonate, brine, dried over anhydrous magnesium sulfate, filtered and concentrated to afford 400 g of crude material. This was chromatographed in 3 batches on a Prep 2000 Chromatogram on silica gel using 20%–50% ethyl acetate/hexane as eluent to yield 320 g of purified material, m/e=674 (M+Li), 98% by HPLC.

Part I: Preparation of N-[2R-hydroxy-3-[[(1,3-benzodioxol-5-yl)sulfonyl](2-methylpropyl)amino]-1S-(phenylmethyl) propyl]-2S-amino-3,3-dimethylbutanamide A solution of 312 g of N-[2R-hydroxy-3-[[(1,3-benzodioxol-5-yl)sulfonyl](2-methylpropyl)amino]-1S-(phenylmethyl) propyl]-2S-[(phenylmethoxycarbonyl)amino]-3,3-dimethylbutanamide in 1 L of tetrahydrofuran was hydrogenated in the presence of 100 g of 4% palladium-on-carbon catalyst under 60 psig of hydrogen for 6 hours at room temperature. The catalyst was removed by filtration and the solvents removed under reduced pressure to afford 240 g of the desired compound.

Part J: Preparation of N-[2R-hydroxy-3-[[(1,3-benzodioxol-5-yl)sulfonyl](2-methylpropyl)amino]-1S-(phenylmethyl) propyl]-2S-[(chloroacetyl)amino]-3,3-dimethylbutanamide To a solution of 234.3 g (0.439 mol) of N-[2R-hydroxy-3-[[(1,3-benzodioxol-5-yl)sulfonyl](2-methylpropyl)amino]-1S-(phenylmethyl) propyl]-2S-amino-3,3-dimethylbutanamide in 1L of methylene chloride, was added 80 mL (59.5 g, 0.46 mol) of diisopropylethylamine, followed by the slow addition at room temperature of 78.8 g (0.46 mol) of chloroacetic anhydride while maintaining the temperature below 35° C. After stirring for an additional 1 hour, analysis by HPLC indicated a small amount of starting material was still present, and 1.5 g of chloroacetic anhydride was added. After 10 minutes, the solvents were removed under reduced pressure, 1 L ethyl acetate added, washed with 5% citric acid, saturated sodium bicarbonate, brine, dried over anhydrous magnesium sulfate, filtered and concentrated to yield 314 g of crude material. This was chromatopheed in 3 portions on a Prep 2000 Chromatogram on silica gel using 20–50% ethyl acetate/hexane to afford 165 g of the desired compound, m/e=616 (M+Li), 98% by HPLC.

Part K: Preparation of N-[2R-hydroxy-3-[[(1,3-benzodioxol-5-yl)sulfonyl](2-methylpropyl)amino]-1S-(phenylmethyl) propyl]-2S-[[(pyrrolidin-1-yl)acetyl]amino]-3,3-dimethylbutanamide To 164.2 g (0.27 mol) of N-[2R-hydroxy-3-[[(1,3-benzodioxol-5-yl)sulfonyl](2-methylpropyl)amino]-1S-(phenylmethyl) propyl]-2S-[(chloroacetyl)amino]-3,3-dimethylbutanamide was added 500 mL of tetrahydrofuran, the solvent removed under reduced pressure to remove any ethyl acetate, and then 350 mL of tetrahydrofuran was added. To this solution at 10° C. was added 130 mL (1.56 mol) of pyrrolidine. After 1 hour, the solvents were removed under reduced pressure, 1 L ethyl acetate added, washed with saturated sodium bicarbonate, brine, dried over anhydrous magnesium sulfate, filtered and concentrated to afford 185 g of crude material, which was assayed by HPLC to be 98.9% purity. This was split into 3 portions and chromatographed on a Prep 2000 Chromatogram using first 50% ethyl acetate/hexane, followed by 5% methanol/ethyl acetate to afford 160 g of purified material (99% by HPLC). This was then recrystallized from 460 mL of diethyl ether and 70 mL of hexane to afford 121 g of the desired product (>99% by HPLC), m/e=651(M+Li), mp=112–114° C.

EXAMPLE 15

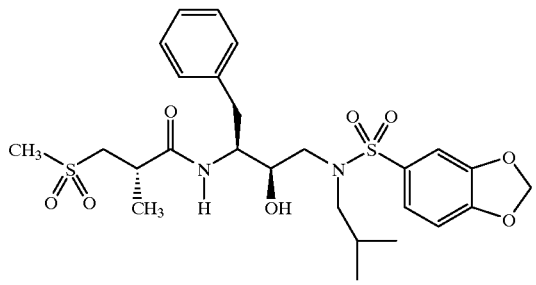

Preparation of N-[2R-hydroxy-3-[(2-methylpropyl)[(1,3-benzodioxol-5-yl)sulfonyl]amino]-1S-(phenylmethyl) propyl]-2S-methyl-3-(methylsulfonyl)propanamide Part A: Preparation of 2(S)-methyl-3-(methylsulfonyl) propionic Acid Step 1: To a solution of 200 g (1.23 mol) of D-(−)-3-acetyl-b-mercaptoisobutyric acid in 1.0 L of methanol, was added 161.0 g (2.47 mol) of potassium hydroxide dissolved in 500 mL of methanol while maintaining the temperature below 10° C. while cooling with an ice bath. After stirring an additional 20 minutes, 117 mL (156 g, 1.23 mol) of dimethyl sulfate was added while maintaining the temperature below 20° C. The ice bath was removed and the mixture stirred for an additional 60 minutes. The salts were removed by filtration, the solvents removed under reduced pressure and ethyl acetate added. After separating the aqueous layer, it was acidified with concentrated hydrochloric acid, extracted with ethyl acetate, dried over anhydrous magnesium sulfate, filtered and concentrated to afford 164 g (99%) of the desired 2S-methyl-3-(methylthio)propionic acid, m/e=133 (M-H).

Step 2: To a solution of 10.0 g (74.6 mmol) of 2S-methyl-3-(methylthio)propionic acid in 150 mL of acetone and 30 mL of water, cooled to 18° C. in an ice bath, was added 161.8 g (263 mmol) of Oxone. After approximately half of material had been added, the temperature rose to 24° C., the addition was stopped, temperature lowered to 18° C., then addition continued. After stirring at 15–20° C. for 15 minutes, the bath was removed and the reaction stirred at room temperature for 1 hour. The solids were filtered and washed with acetone, the filtrate concentrated to approximately 40 mL and the residue dissolved in 200 mL of ethyl acetate. The ethyl acetate layer was dried with anhydrous magnesium sulfate, filtered and concentrated to afford 11.4 g of an oil. This was dissolved in a minimum of ethyl acetate and hexane added to cause a precipitate to form. This was collected to afford 6.95 g of the desired product, m/e=167 (M+H).

Part B: Preparation of N-[2R-hydroxy-3-[(2-methylpropyl) [(1,3-benzodioxol-5-yl)sulfonyl]amino]-1S-(phenylmethyl) propyl]-2S-methyl-3-(methylsulfonyl) propanamide To a solution of 5.0 g (30 mmol) of 2S-methyl-3-(methylsulfonyl)propionic acid and 6.90 g (45 mmol) N-hydroxybenzotriazole in 30 mL of anhydrous DMF at 0° C. under nitrogen, was added 6.34 g (33 mmol) of EDC. After approximately 10 minutes, the EDC was all dissolved. After 60 minutes at 0° C., a solution of 15.5 g (30 mmol) of 2R-hydroxy-3-[[(1,3-benzodioxol-5-yl)sulfonyl](2-methylpropyl)amino]-1S-(phenylmethyl)propylamine methanesulfonate in 30 mL of anhydrous DMF, previously neutralized with 3.4 mL (31.6 mmol) of 4-methylmorpholine, was added. After 3 hrs at 0° C., the mixture was then stirred overnight for 17 hrs. The DMF was removed under reduced pressure, ethyl acetate added, washed with 5% citric acid, saturated sodium bicarbonate, water, brine, dried over anhydrous magnesium sulfate, filtered and concentrated to afford 16 g of crude material, which was 88% pure by HPLC. The product was chromatographed on silica gel using 20%–80% ethyl acetate/hexane to afford the pure product, which was recrystallized from ethyl acetate/hexane to afford 8.84 g of pure product, mp 131.8–133.8° C.

Alternatively, to a solution of 35.0 g (211 mmol) of 2S-methyl-3-(methylsulfonyl)propionic acid and 48.3 g (315 mmol) N-hydroxybenzotriazole in 210 mL of anhydrous DMF at 0° C. under nitrogen, was added 44.4 g (231 mmol) of EDC. After approximately 30 minutes, the EDC was all dissolved. After an additional 60 minutes at 0° C., a solution of 108.8 g (211 mmol) of 2R-hydroxy-3-[[(1,3-benzodioxol-5-yl)sulfonyl](2-methylpropyl)amino]-1S-(phenylmethyl)propylamine methanesulfonate in 350 mL of anhydrous DMF, previously neutralized with 24 mL (22.3 g) of 4-methylmorpholine, was added. After 2 hrs at 0° C., the mixture was then stirred overnight for 18 hrs. The DMF was removed under reduced pressure, 1 L of ethyl acetate added, washed with 5% citric acid, saturated sodium bicarbonate, water, brine, dried over anhydrous magnesium sulfate, filtered and concentrated to afford 120.4 g of crude material, which was 90% purity by HPLC. The product was crystallized twice from 750–1000 mL of absolute ethanol to afford 82.6 g of the desired product.

EXAMPLE 16

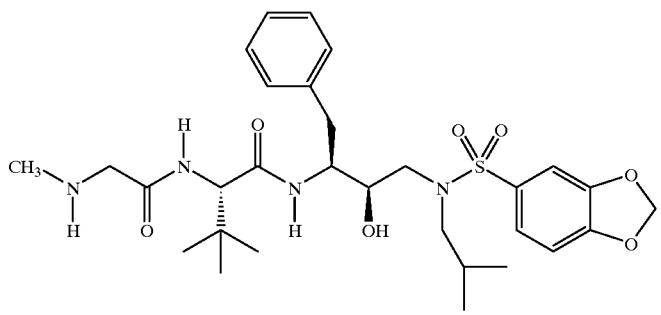

Preparation of 2S-[[(N-methylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide To 6.55 g (10.7 mmol) of N-[2R-hydroxy-3-[[(1,3-benzodioxol-5-yl)sulfonyl](2-methylpropyl)amino]-1S-(phenylmethyl)propyl]-2S-[(chloroacetyl)amino]-3,3-dimethylbutanamide was added 25 mL of tetrahydrofuran, the solvent removed under reduced pressure to remove any ethyl acetate, and then 25 mL of tetrahydrofuran was added. To this solution at 10° C. was added 19 mL (214 mmol) of 40% aqueous methylamine. After 2 hours, the solvents were removed under reduced pressure, added 1 L ethyl acetate, washed with saturated sodium bicarbonate, brine, dried over anhydrous magnesium sulfate, filtered and concentrated to afford 6.0 g of product (98% purity).

EXAMPLE 17

Retroviral protease in hibitor compounds of the present invention are effective HIV protease inhibitors. The enzyme assay described below can be used in the selection of retroviral protease inhibitors for use in combination therapy. The IC50 (the concentration at which the inhibitor compound reduces enzyme activity by 50%) for such compounds can be calculated using this method.

The enzyme method is as follows. The substrate is 2-aminobenzoyl-Ile-Nle-Phe (p-NO2)-Gln-ArgNH2. The positive control is MVT-101 (Miller, M. et al, Science 246, 1149 (1989)). The assay buffer is 20 mM sodium phosphate, pH 6.4, 20% glycerol, 1 mM EDTA, 1 mM DTT and 0.1% CHAPS. The substrate is dissolved in DMSO, then diluted 10 fold in assay buffer. Final substrate concentration in the assay is about 80 $\mu$M. HIV protease is diluted in the assay buffer to a final enzyme concentration of about 12.3 nanomolar, based on a molecular weight of 10,780.

The final concentration of DMSO is about 14% and the final concentration of glycerol is about 18%. The test compound is dissolved in DMSO and diluted in DMSO to about ten times (10x) the test concentration, then 10 $\mu$L of substrate. The increase in fluorescence is monitored at 4 time points (0, 8, 16 and 24 minutes) at ambient temperature. Each assay is carried out in duplicate wells.

EXAMPLE 18

The effectiveness of selected HIV protease inhibitor compounds of the present invention can be determined using the above-described enzyme assay and the following CD4+ cell line assay. Antiviral activities of protease inhibitors are expressed as effective concentration 50 ($EC_{50}$) and/or effective concentration 90 ($EC_{90}$) values. These are the concentrations of inhibitors that were required to inhibit viral replication by 50% or 90%, respectively.

The HIV inhibition assay method of acutely infected cells is an automated tetrazolium based calorimetric assay essentially that reported by Pauwels et al, J. Virol. Methods 20, 309–321 (1988). Assays are performed in 96-well tissue culture plates. A CD4+ cell line, such as CEM, MT-2, MT-4 and the like cell lines, is grown in RPMI-1640 medium (Gibco) supplemented with a 10% fetal calf serum and are then treated with polybrene (2 $\mu$g/ml). An 80 $\mu$l volume of medium containing $1\times10^4$ cells is dispensed into each well of the tissue culture plate. To each well is added a 100 $\mu$l volume of test compound dissolved in tissue culture medium (or medium without test compound as a control) to achieve the desired final concentration and the cells are incubated at 37° C. for 1 hour. A frozen culture of HIV-1 is diluted in culture medium to a concentration of $5\times10^4$ $TCID_{50}$ per ml ($TCID_{50}$=the dose of virus that infects 50% of cells in tissue culture), and a 20 $\mu$L volume of the virus sample (containing 1000 $TCID_{50}$ of virus) is added to wells containing test compound and to wells containing only medium (infected control cells). Several wells receive culture medium without virus (uninfected control cells). Likewise, the intrinsic toxicity of the test compound is determined by adding medium without virus to several wells containing test compound. In summary, the tissue culture plates contain the following experiments:

|    | Cells | Drug | Virus |
| --- | --- | --- | --- |
| 1. | + | − | − |
| 2. | + | + | − |
| 3. | + | − | + |
| 4. | + | + | + |

In experiments 2 and 4 the final concentrations of test compounds are 1, 10, 100 and 500 $\mu$g/ml. Either azidothymidine (AZT) or dideoxyinosine (ddI) is included as a positive drug control. Test compounds are dissolved in DMSO and diluted into tissue culture medium so that the final DMSO concentration does not exceed 1.5% in any case. DMSO is added to all control wells at an appropriate concentration.

Following the addition of virus, cells are incubated at 37° C. in a humidified, 5% $CO_2$ atmosphere for 7 days. Test compounds can be added on days 0, 2, and 5 if desired. On day 7, post-infection, the cells in each well are resuspended and a 100 $\mu$l sample of each cell suspension is removed for assay. A 20 $\mu$L volume of a 5 mg/ml solution of 3-(4,5- dimethylthiazol-2-yl)-2,5-diphenyltetrazolium bromide (MTT) is added to each μL cell suspension, and the cells are incubated for 4 hours at 37° in a 5% $CO_2$ environment. During this incubation, MTT is metabolically reduced by living cells resulting in the production in the cell of a colored formazan product. To each sample is added 100 μl of 10% sodium dodecylsulfate in 0.01N HCl to lyse the cells, and samples are incubated overnight. The absorbance at 590 nm is determined for each sample using a Molecular Devices microplate reader. Cytotoxicity and antiviral efficacy of the test compound is determined by comparison of the absorbance values obtained in wells containing infected or uninfected cells incubated with compounds and the uninfected, untreated control wells.

HIV CULTURE PROCEDURES

Stimulation of Donor Lymhocytes

Buffy coats were obtained from the American Red Cross or Blood Bank at Washington University School of Medicine. These preparation are pre-screened for HIV and CMV antibodies and HBV surface antigen (HBsAg) and ALT (alanine transferase activity) as marker for non-A, non-B hepatitis. Leukocyte-enriched blood (30 ml) is removed from the plastic container and 15 ml is dispensed into two 50 ml screw-cap centrifuge tubes. Each sample is diluted with an equal volume of sterile PBS and mixed by pipeting. Ficoll-Paque (15 ml) or LSM is placed below the diluted blood samples using a Pasteur pipet and allowing the solution to drain to the bottom of the tube. Each of the tubes is then centrifuged at 1300 rpm (400×g) for 45 minutes at 20° C. Following centrifugation, the lymphocyte band at the interface is removed and transferred to a 50 ml tube. Sterile PBS is added to dilute the separated lymphocytes and then centrifuged at 1300 rpm for 8 minutes. The cell pellet is washed two times by resuspending in PBS and recentrifuging. The final cell pellet is resuspended in 20 ml PBS by pipetting and the total number of viable cells is determined by Trypan Blue exclusion.

Acute Infectivity Assays Using Clinical Isolates

Approximately $3 \times 10^7$ cells are activated for 48 hours with about 3–5 μg/ml PHA in RPMI continuing 10% fetal bovine serum and IL-2 (10 U/ml). Quantitated virus stocks are added to the activated lymphocyte suspension at a multiplicity of infection of about 0.001–0.01. The cell-virus suspension is incubated at 37° C. for 2 hours to allow virus absorption. The residual virus inoculum is removed by centrifugation and the cells are resuspended in RPMI containing 10% FBS and 10 U/ml IL-2. These infected cells are added to the test-article diluted in complete tissue culture medium from a stock (10 mg/ml) in DMSO in 96 well microtiter plates to give about $5 \times 10^5$ cells per well per 200 μl. Infected, untreated cells and cells treated with DMSO alone (0.1%) or either AZT or DDI were used as controls. The cultures were examined for syncytia formation on days 7 and 11 post-infection or the supernatants tested for reverse transcriptase activity or p24 antigen.

Chronic Infectivity Assays

CEM cells chronically infected with HXB2 (laboratory strain of HIV-1) are added to six wells of a 12 well microtiter plate to give about $5 \times 10^4$ cells per well. Half of the wells are treated with test compound at various concentrations and the same number of uninfected CEM cells are maintained without added compound. Fresh medium with or without test compound is added each day for three consecutive days. The cultures are then incubated for 48 hours without a change in the medium. The cells are harvested by centrifugation, washed 2× in PBS and resuspended in 50 μl 2× Laemmli buffer containing 0.125M Tris pH 6.8, 4% SDS, 20% glycerol, 10% beta mercaptoethanol and 0.02% Bromophenol blue. Culture supernatants are passed through a 0.22 μm filter to remove cell debris and the centrifuged at 50,000 rpm for 90 minutes to concentrate the virus particles. The virus pellet is resuspended in 50 μl 2× Lammli buffer. The cell or virus suspensions are boiled for 5 minutes and then subjected to electrophoretic separation in a 10–20% SDS-polyacrylamide gradient gel. Contents of the gel are then transferred onto nitrocellulose by electroblotting. HIV specific proteins are detected using monoclonal antibodies to p24 and p17 followed by goat-anti-mouse IgG linked to biotin, and avidin linked to HRP. Enzymatic conversion of 4-chloro-1-naphthol was used to visualize the specific proteins recognized by the monoclonal antibodies. In addition, the infectivity of virus produced by the chronically infected CEM cells in the presence or absence or the test compounds was examined. Filtered supernatants are serially diluted and used to infect uninfected CEM cells (about $1 \times 10^4$/well). The cultures were examined for syncytia formation on days 7 and 11 post-infection or the supernatants tested for reverse transcriptase activity or p24 antigen.

Micro Reverse Transcriptase (RT) Assay

The micro RT assay is an adaptation of several standard RT assays. It was developed to allow small volume quantitative measurement of HIV RT activity and to facilitate processing of numerous samples.

| MATERIALS | STOCK | WORKING SOLUTION (per 1 ml) |
|---|---|---|
| Tris (pH 7.8) | 1.0 M | 50 μl |
| KCl | 3.0 M | 25 μl |
| DTT (store −20° C.) | 0.1 M | 20 μl |
| $MgCl_2$ | 0.15 M | 33 μl |
| poly (rA)p(dT012-18) | 25 U/2.5 ml | 25 μl |
| Pharmacia 27-7878 | | (0.5 U) |
| NP-40 | 2% | 25 μl |
| $^3$H-TTP | 2.5 Ci/ml | 10 μl |
| (NET 221A, 80 Ci/mmol) | | |
| $H_2O$ | | 777 μl |

Method:

1. Add 50 μl RT cocktail per well into a 96-well U-bottom microtiter plate.
2. Add 10–20 μl per well of cell-free supernatant solution.
3. Mix well using mechanical rotator.
4. Incubate at 37° C. for 2 hours.
5. Aspirate onto DE81 filter paper, or equivalent, using TOMTEK.
6. Rinse using 2X SSC four times.
7. Rinse using 95% Ethanol once.
8. Dry filter.
9. Prepare for counting using Beta-plate counter (Pharmacia).

EXAMPLE 19

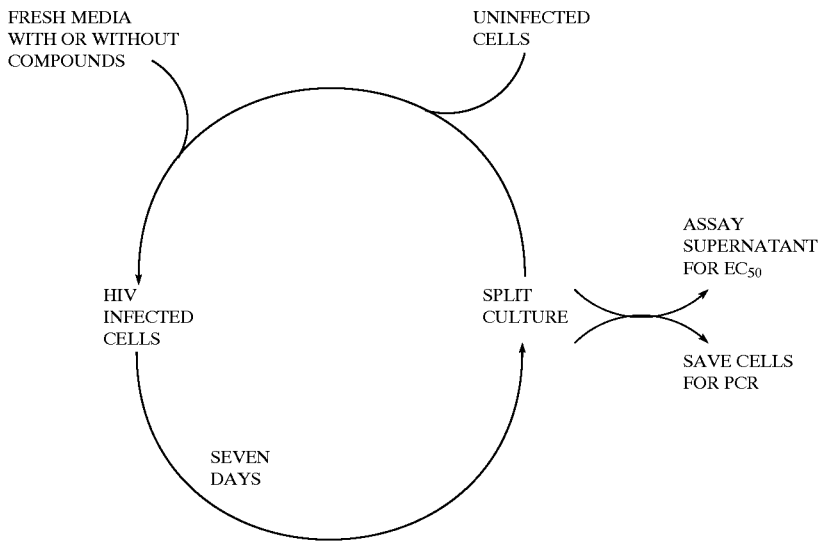

The following is the culture method used for selection of HIV protease inhibitor resistant mutants. Infected cells were grown continually in the presence of protease inhibitor. Some cultures were subjected on alternate weeks to high and low inhibitor concentrations. Others were passaged in a constant concentration. Drug concentrations were increased periodically until a consistent shift in the $EC_{50}$ was observed. A shift in the dose response curve was generally detected at drug concentration of 0.5 to 1 μg/ml or greater (5–10× the $EC_{90}$) and depended on the viral isolate being treated. Both laboratory adapted and primary clinical isolates of HIV were used. The same virus isolates were passaged in the same way in the absence of drugs so that direct nucleoside sequence comparisons could be made between treated and untreated isolates. Generally, HIV-1 variants resistant to protease inhibitors were select by serial passage (growth) in the presence of several inhibitory concentrations of the protease inhibitor specified (see Markowitz et al., Journal of Virology 69:701–706 (1995)). The HIV-1 variants listed below indicate the mutations which are present in the selected virus isolates and not present in the control, untreated virus isolates.

RF represents the HIV-1 strain HIV-lRF and RFR represents a mixture of resistant strains obtained by selection of RF against the compound of Example 1. RFR comprises a mixture of viral strains having protease genotypes of G48V (14/40 clones); G48V, V82A (18/40 clones); G48V, L90S (2/40 clones); G48V, I54T, V82A (1/40 clones); G48M (1/40 clones); G48V, Q61H (1/40 clones); V13I, G48V (1/40 clones); G48V, F53L, V82A (1/40 clones); and G48V, V82A, C95Y (1/40 clones). RFR2 represents a mixture of resistant strains obtained by cloning RFR by three rounds of growth at limiting dilution. RFR2 comprises a mixture of viral strains having protease genotypes of G48V, V82A (13/15 clones); G17E, G48V, V82A (1/15 clones); and G48V, V82A, N37D, N88D (1/15 clones). RFRR represents a mixture of resistant strains obtained by selection of RF against the compounds of Examples 1 and 2 and then cloning by three rounds of growth at limiting dilution. RFRR comprises a mixture of viral strains having protease genotypes of G48V, I54T, L63P, V82A (7/9 clones); G48V, I54T, L63P, V82A, N88S (1/9 clones); and G48V, I54T, L63P, G73M, V82A (1/9 clones). SF162 represents the HIV-1 strain SF-162 and SF162R represents a mixture of resistant strains obtained by selection of SF162 against the compound of Example 1. SF162R comprises a mixture of viral strains having protease genotypes of M46I, F53L, L63P, A71V, N88D (2/3 clones); and M46I, F53L, L63P, A71V, N88D, Q92R (1/3 clones). 89–959 represents the HIV-1 strain 89–959 and 89–959R represents a mixture of resistant strains obtained by selection of 89–959 against the compound of Example 2. 89–959R comprises a mixture of viral strains having protease genotypes of N88S (4/5 clones); and D25N, T26A, D30N, D37N, R41K, G73D, R87K, N88S (1/4 clones). NL4 represents the HIV-1 strain $HIV\text{-}1_{NL4\text{-}3}$. NL4(G48V) represents a strain having a synthetically generated site-directed mutation in the protease from glycine to valine at amino acid position number 48. NL4(I84V) represents a strain having a synthetically generated site-directed mutation in the protease from isoleucine to valine at amino acid position number 84. NL4(R8Q,M46I) represents a strain having synthetically generated site-directed mutations in the protease from arginine to glutamine at amino acid position number 8 and methionine to isoleucine at amino acid position number 46. NL4(P22-538) represents a mixture of resistant strains obtained by selection of $HIV\text{-}1_{NL4\text{-}3}$ against the compound of Example 10 after 22 passages comprising protease genotypes M46I, L63P, A71V, V82F, I84V (4/10); M46I, L63P, V82F, I84V (3/10); and M46I, A71V, V82F, I84V (3/10). NL4(P37-538) represents resistant strains obtained by selection of $HIV\text{-}1_{NL4\text{-}3}$ against the compound of Example 10 after 37 passages comprising protease genotype M46I, L63P, A71V, I84A. NL4(538/524) represents resistant strains obtained by selection of NL4 (P22-538) against the compound of Example 5 after 24 passages comprising protease genotype M46I, L63P, A71V, I84A. NL4(538/P7-AG) represents a mixture of resistant strains obtained by selection of NL4(P22-538) against the compound of Example 12 after 7 passages comprising protease genotypes M46I, L63P, A71V, I84A; and V32I, V82I. NL4(538/P24-AG) represents resistant strains obtained by selection of NL4(P22-538) against the compound of Example 12 after 24 passages comprising protease genotype M46I, L63P, A71V, I84A. NLA(P19-003) represents resistant strains obtained by selection of $HIV\text{-}1_{NL4\text{-}3}$ against the compound of Example 9 after 19 passages comprising protease genotype R8K, M46I. NL4(P34-003) represents resistant strains obtained by selection of HIV-$1_{NL4-3}$ against the compound of Example 9 after 34 passages comprising protease genotype R8K, M46I, L63P, A71V, L90M. Viral isolate resistance results are summarized in Tables 1–11.

EXAMPLE 20

The viral isolate resistance results summarized in Tables 1–3 were generated according to the following assay procedure or minor modifications thereof. Approximately $3 \times 10^7$ cells are activated for 48 hours with about 3–5 fg/ml PHA in RPMI continuing 10% fetal bovine serum and IL-2 (10 U/ml). Quantitated virus stocks are added to the activated lymphocyte suspension at a multiplicity of infection of about 0.001–0.01. The cell-virus suspension is incubated at 37° C. for 2 hours to allow virus absorption. The residual virus inoculum is removed by centrifugation and the cells are resuspended in RPMI containing 10% FBS and 10 U/ml IL-2. These infected cells are added to the test-compound diluted in complete tissue culture medium from a stock (10 mg/ml) in DMSO in 96 well microtiter plates to give about $5 \times 10^5$ cells per well per 200 μl. Infected, untreated cells and cells treated with DMSO alone (0.1%) or either AZT or DDI were used as controls. The cultures were examined for syncytia formation on days 7 and 11 post-infection or the supernatants tested for reverse transcriptase activity or p24 antigen.

TABLE 1

| Ex. | Virus Isolate ($EC_{50}$ ng/mL) | |
|---|---|---|
| No. | SF162 | SF162R |
| 1 | 31 | 443 |
| 2 | 2 | 6 |
| 5 | 4 | 4 |
| 6 | 2 | 11 |

TABLE 2

| Ex. | Virus Isolate ($EC_{50}$ ng/mL) | |
|---|---|---|
| No. | SF162 | SF162R |
| 1 | 2 | 111 |
| 7 | 1 | 108 |
| 8 | 1 | 98 |

TABLE 3

| Ex. | Virus Isolate ($EC_{50}$ ng/mL) | | |
|---|---|---|---|
| No. | 89-959 | 89-959R | 89-959R |
| 1 | 96† | 5† | 37‡ |
| 2 | 100† | 395† | 872‡ |
| 5 | 36† | 5† | 38‡ |
| 6 | 4 | | 6‡ |
| 7 | 13§ | 12§ | |
| 8 | 12§ | 11§ | |

†, ‡, §Indicates values obtain in the same experiment

EXAMPLE 21

The viral isolate resistance results summarized in Tables 4–6 were generated according to the following assay procedure or minor modifications thereof. Assays are performed in 96-well tissue culture plates. CEM-T4 cells are suspended in 90% RPMI media (Gibco BRL Life Technologies, Inc., Gaithsburg, Md.) 10% heat-treated, fetal bovine serum (Gibco BRL Life Technologies, Inc., Gaithsburg, Md.) to a final concentration of $5 \times 10^5$ viable cells per ml. A frozen aliquot of an HIV culture (strain HIV-$1_{RF}$) is thawed rapidly (in a 37° C. water bath) and added to the CEM-T4 cells to give a final concentration of about 0.001–0.01 infectious units per cell. The virus-cell suspension is rapidly mixed by swirling and 100 μL immediately added to 100 μL of each test-compound (prepared as a 2× concentrate in 90% RPMI, 10% FBS) dilution in each well of a 96-well tissue culture plate. Each plate contains control wells that comprise cells and virus but no test-compound. 3'-Azido-3'-deoxythymidine (AZT) is included as a positive control in all assays.

The tissue culture plates are incubated at 37° C. in a humidified, 5% $CO_2$ atmosphere for 7 days. The level of viral replication is then determined by measurement of reverse transcriptase activity in the supernatents using standard methods (as previously described and see, for example, Techniques in HIV Research, Aldovini & Walker, eds., 1990, Stockton Press, NY).

TABLE 4

| Ex. | Virus Isolate ($EC_{50}$ ng/mL) | |
|---|---|---|
| No. | RF | RFR |
| 1 | 30 | 223† |
| 2 | 40 | 8† |
| 3 | 5 | 2† |
| 4 | 10 | 0.4† |
| 5 | 44‡ | 7† |
| 6 | 12‡ | 15† |

†, ‡Indicates values obtain in the same experiment

TABLE 5

| Ex. | Virus Isolate ($EC_{50}$ ng/mL) | |
|---|---|---|
| No. | RF | RFR |
| 1 | 24 | 394 |
| 7 | 2 | 78 |
| 8 | 2 | 1 |

TABLE 6

| Ex. | Virus Isolate ($EC_{50}$ ng/mL) | | |
|---|---|---|---|
| No. | RF | RFR2 | RFRR |
| 1 | 19 | 880 | 5609 |
| 2 | 35 | 367 | 1111 |
| 5 | 6 | 57 | 982 |
| 6 | 6 | 31 | 962 |
| 14 | 1 | 6 | 39 |
| 15 | 5 | 9 | 21 |
| 16 | 3 | 1 | 9 |

EXAMPLE 22

The viral isolate resistance results summarized in Tables 7–11 were generated according to the assay procedures described by Markowitz et al., Journal of Virology, vol. 69, 701–706 (1995), which is incorporated herein by reference in its entirety, or minor modifications thereof.

TABLE 7

| Ex. | Virus Isolate (EC$_{90}$ nM) | | |
|---|---|---|---|
| No. | NL4 | NL4(G48V) | NL4(I84V) |
| 5 | 80 | 160 | 640 |
| 6 | 30 | 150 | 90 |
| 10 | 80 | 160 | 800 |
| 12 | 25 | 125 | 125 |
| 13 | 250 | 1000 | 6250 |
| 14 | 8 | 8 | 72 |
| 15 | 60 | 60 | 60 |
| 16 | 8 | 8 | 8 |

TABLE 8

| Ex. | Virus Isolate (EC$_{50}$ nM) | |
|---|---|---|
| No. | NL4 | NL4(R8O,M46I) |
| 5 | 80 | 240 |
| 6 | 30 | 30 |
| 10 | 80 | 240 |
| 12 | 25 | 125 |
| 13 | 250 | 750 |
| 16 | 8 | 8 |

TABLE 9

| Ex. | Virus Isolate (EC$_{50}$ nM) | | |
|---|---|---|---|
| No. | NL4 | NL4(P22-538) | NL4(P37-538) |
| 5 | 80 | 800 | 6400 |
| 6 | 30 | 150 | 2400 |
| 10 | 80 | 1600 | 6400 |
| 12 | 25 | 500 | >3125 |
| 13 | 250 | 5000 | >31250 |
| 14 | 60 | 60 | 1000 |
| 15 | 8 | 400 | 1000 |
| 16 | 8 | 8 | 40 |

TABLE 10

| Ex. | Virus Isolate (EC$_{50}$ nM) | | | |
|---|---|---|---|---|
| No. | NL4 | NL4(538/524) | NL4(538/P7-AG) | NL4(538/P24-AG) |
| 5 | 80 | 6400 | 6400 | 6400 |
| 6 | 30 | 2400 | 2400 | 2400 |
| 10 | 80 | 6400 | 6400 | 6400 |
| 12 | 25 | >3125 | >3125 | >3125 |
| 13 | 250 | >31250 | >31250 | >31250 |
| 16 | 8 | 40 | 40 | 40 |

TABLE 11

| Ex. | Virus Isolate (EC$_{50}$ nM) | | |
|---|---|---|---|
| No. | NL4 | NLA(P19-003) | NL4(P34-003) |
| 5 | 80 | 240 | 400 |
| 6 | 30 | 30 | 30 |
| 10 | 80 | 400 | 400 |
| 12 | 25 | 150 | 375 |
| 13 | 250 | 1250 | 1250 |
| 16 | 8 | 8 | 8 |

EXAMPLE 23

Protease inhibitors of Examples 1 and 2, which contain a unique hydroxyethylurea isostere, were used to select drug resistant HIV-1 variants in vitro. Clinical and laboratory HIV-1 strains were passaged in T cell lines or peripheral blood mononuclear cells (PBMCs) in the presence of increasing drug concentrations. Resistant variants consistently exhibited EC$_{50}$ values at least 10-fold higher than control virus passaged for an identical period, but in the absence of an inhibitor. Viral DNA was amplified by PCR and the nucleotide sequence of the gene encoding the protease was determined using standard methods. In viruses resistant to protease inhibitors of Examples 2 and 1, respectively, an amino acid change at position 88 was consistently observed in many of the variants selected. The Asn residue at 88 lies within a structurally conserved helical domain, present in both monomeric and dimeric aspartic proteinases. The corresponding carboxy terminal sequence Gly-Arg-Asp/Asn (residues 86–88) is unique to retroviral aspartic proteinases. While any explanation for these results is only speculation, modeling studies based on templates derived from high resolution x-ray structures of prototypical hydroxyethylurea inhibitors bound to recombinant HIV-1 protease appear to suggest that the Asn88 mutations may alter the conformation of the protease.

Retroviral protease inhibitor compounds of the present invention are advantageously effective antiviral compounds and, in particular, are effective inhibitors of retroviruses, particularly, lentiviruses as shown above. Thus, the subject compounds are effective inhibitors of HIV. It is contemplated that the subject compounds will also inhibit other strains of HIV, such as HIV-2 and other viruses such as, for example, VISNA virus and Simian Immunodeficiency virus (SIV), HTLV-1 and HTLV-2. Thus, the subject compounds are effective in the treatment and/or prophylaxis of retroviral infections.

The present invention is also meant to include the solvate or hydrates of the retroviral protease inhibitor compounds, when possible, and are prepared or isolated by methods known in the art.

The retroviral protease inhibitor compounds can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid preferably hydrochloride salt. Other examples include salts with alkali metals or alkaline earth metals, such as sodium, potassium, calcium or magnesium or with organic bases.

Total daily dose administered to a host in single or divided doses may be in amount, for example, from 0.01 to 50 mg/kg body weight daily and more usually 0.1 to 30 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the retroviral protease inhibitor compounds and/or compositions is selected in accordance with a variety of factors, including the type, age, weight, sex, diet and medical condition of the patient, the severity of the disease, the route of administration, pharmacological consideration such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable siluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, the fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least on inert diluent such as sucrose, lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the retroviral protease inhibitor compounds of the present invention can be administered as the sole active pharmaceutical agents, they can also be used in combination with other antiviral agents which are effective against retroviruses such as HIV-1. Such compounds include, but are not limited to, other HIV-1 protease inhibitors, various nucleoside analogs, nonnucleoside reverse transcriptase inhibitors, tat antagonists and glycosidase inhibitors.

Examples of HIV-1 protease inhibitors include, but not limited to, Ro 31-859 (Roberts, N. A. et al. Science 1990, 248, 258–261 and Drugs of the Future 1991, 16(3), 210–212, KNI-272, (Kagayama, S., et al. Antimicrobial Agents and Chemotherapy 1993, 810–817), the cyclic urea series (Lam, P., et al., "De Novo Design and Discovery of Potent, Nonpeptidal HIV-1 Protease Inhibitors," paper 96 at the 205th American Chemical Society National Meeting, Medicinal Chemistry Division, Denver, CO, Mar. 28–Apr. 2, 1993), L-735,524 (Dorsey, B. D., et al., "L-735,524: The Rational Design of a Potent and Orally Bioavailable HIV Protease Inhibitor," paper 6 at the 206th American Chemical Society National Meeting, Medicinal Chemistry Division, Chicago, Ill., Aug. 22–27, 1993) and analogs thereof.

Examples of competitive nucleoside analogs include, but are not limited to, azidothymidine (AZT), dideoxyinosine (DDI), DDC, 3TC, D4T and PMEA. Examples of non-nucleoside, non-competitive reverse transcriptase inhibitors include, but are not limited to, the pyridone class (Wei, J. S., et al. J. Med. Chem. 1993, 36, 249–255; Hoffman, J. M., et al. J. Med. Chem. 1992, 35, 3784–3791; Saari et al. J. Med. Chem. 1992, 35 3792–3802; Drugs of the Future 1992, 17(4), 283–285, and analogs thereof); the bis-(heteroaryl) piperazines class (Romero, D. L., et al. J. Med. Chem. 1993, 36, 1505–1508; Romero, D. L., et al. Proc. Natl. Acad. Sci. USA 1991, 34, 746–751 and 3187–3198; and analogs thereof) and the tricyclic pyridobenzo- and depyridodiazepinones (Hargrave, K. D., J. Med. Chem. 1991, 34, 2231–2241; Merluzzi, M. J. Science 1990, 250, 1411–1413; and analogs thereof) and 5-chloro-3-(phenylsulfonyl)indole-2-carboxamide and its analogs (Williams, T. M. et al., J. Med. Chem. 1993, 36, 1291–1294). Examples of tat antagonists include, but are not limited to, Ro 5-3335 and Ro 24-7429 (Hsu, M. C. et al., Proc. Natl. Acad. Sci. USA 1993, 909, 6395–6399; Tam, S. et al., "TAT INHIBITORS: A NEW CLASS OF ANTI-HIV AGENTS," paper 372, at the 204th American Chemical Society National Meeting, Organic Chemistry Division, Washington, D.C., Aug. 23–28, 1992) and analogs thereof. Examples of glycosidase inhibitors include, but are not limited to, castanospermine, castanospermine 6-butryl ester, N-butyl-1-deoxynojirimycin, N-butyl-1-deoxynojirimycin per-butryl ester and analogs and prodrugs thereof.

The therapeutic agents can be formulated as separate compositions which are given at substantially the same time or the therapeutic agents can be given as a single compositions such that all of the active agents are at a therapeutically effective amount in the host. Alternatively, the therapeutic agents can be administered to the host at different times such that only one or two active agents at a time are at a therapeutically effective amount in the host.

The compounds and methods of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, rous sarcoma virus, simian immunodeficiency virus, feline leukemia virus, feline immunodeficiency virus and the like. Thus, the subject compounds are effective in the treatment and/or proplylaxis of retroviral infections.

The subject compounds and methods are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently or unknowingly be present in the cell culture. The virus may be present originally in the cell culture, for example HIV is known to be present in human T-lymphocytes long before it is detectable in blood, or through exposure to the virus. This use of the subject compounds and methods prevent the unknowing or inadvertent exposure of a potentially lethal retrovirus to a researcher or clinician.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Method of treating retroviral infections in a mammal comprising administering to said mammal:
   (a) an effective amount of a first retroviral protease inhibitor; and
   (b) an effective amount of a second retroviral protease inhibitor wherein said second retroviral protease inhibitor is effective against at least one retroviral strain that is resistant to said first retroviral protease inhibitor.

2. A method of treating a retroviral infection in a mammal comprising administering retroviral protease inhibitors to said mammal in a pharmaceutically effective amount, said retroviral protease inhibitors consisting of a first retroviral protease inhibitor and a second retroviral protease inhibitor) wherein said second retroviral protease inhibitor is effective against at least one retroviral strain that is resistant to said first retroviral protease inhibitor, and wherein said first and second inhibitors are selected from the group consisting of:

N-(2(R)-Hydroxy-1(S)-indanyl)-2(R)-phenylmethyl-4 (S)-hydroxy-5-1(1-(4-(3-pyridylmethyl)-2(S)-N'-(t-butylcarboxamido)-piperazinyl))-pentaneamide;

N-tert-Butyl decahydro-2-[2(R)-hydroxy-4-phenyl-3(s)-[[N-(2-quiolylcarbonyl)-L-asparaginyl]amino]butyl] (4aR, 8aS)-isoquinoline-3(S)-carboxamide;

(2S, 3R, 4S, 5S)-2,5-Bis-[N-[N-[[N-methyl-N-(2-pyridinylmethyl)amino]carbonyl]valinyl]amino]-3,4-dihydroxy-1,6-diphenylhexane;

(2S, 3S, 5S)-5-[N-[N-[N-[N-methyl-N[(2-isopropyl-4-thiazolyl)methyl]amino)carbonyl]valinyl]amino]-2-[N-[(5-thiazolyl)methoxycarbonyl]amino]-3-hydroxy-1,6-diphenylhexane;

N-tert-Butyl decahydro-2-[2(R)-hydroxy4-(phenylthio)-3 (S)-[N-[(2-methyl-3-hydroxyphenyl)carbonyl]amino] butyl]-(4aR, 8aS)-isoquinoline-3(S)-carboxamide;

[4R-(4α, 5α, 6β 7β)]-1,3-bis](3-aminophenyl)methyl] hexahydro-5,6-dihydroxy-4,7-bis(phenylmethyl)-2H-1,3-diazepin-2-one;

N-[2R-hydroxy-3-[[(1,3-benzodioxol-5-yl)sulfonyl](2-methylpropyl)amino]-1S-phenylmethyl)propyl]-2S-[[(pyrrolidin-1-yl)acetyl]amino]-3,3-dimethylbutanamide;

N-[2R-hydroxy-3-[(2-methylpropyl)[(1,3-benzodioxol-5-yl) sulfonyl]amino]-1S-)phenylmethyl)propyl]-2S-methyl-3-(methylsulfonyl)propanamide;

[1S-[1R"(R"), 2S"]]-N-[2-hydroxy-3-[N$^1$-(2-methylpropyl)-N$^1$-(4methoxyphenylsulfonyl)amino]-1-(phenylmethyl) propyl]-2-methyl-3-(methylsulfonyl) propanamide;

2S-[[(N-methylamino)acetyl]amino]-N-[2R-hydroxy-3-[[(1,3-benzodioxol-5-yl)sulfonyl](2-methylpropyl) amino]2S-(phenylmethyl)propyl]-3,3-dimethylbutanamide; and (2R, 3S)-3-(N-methylaminoacetyl-L-tert-butylglycinyl) amino-1-(N-isoanyl-N-(tert-butylcarbamoyl))amino-4-phenyl-2-butanol.

3. Method of claim 1 further comprising administration of at least one antiviral agent other than a protease inhibitor.

4. Method of claim 3 wherein said antiviral agent is a nucleoside analog, nonnucleoside reverse transcriptase inhibitor, tat antagonist or glycosidase inhibitor.

5. Method of claim 4 wherein said nucleoside analog is AZT, DDI, DDC, 3TC, D4T or PMEA and said glycosidase inhibitor is castanospermine or N-butyl-1-deoxynojirmycin.

6. Method of claim 1 wherein said mammal is a human, monkey or cat.

7. Method of claim 1 wherein said retrovirus is HIV or HTLV.

8. Method of claim 7 wherein said retrovirus is HIV-1 or HIV-2.

* * * * *